US006585507B1

(12) United States Patent
Kalidindi

(10) Patent No.: US 6,585,507 B1
(45) Date of Patent: Jul. 1, 2003

(54) SAMPLING DIE AND PRESS FOR COMPACTION OF POWDER SAMPLE

(76) Inventor: Sanyasi R. Kalidindi, 15 Edinburg La., East Brunswick, NJ (US) 08816-5242

( * ) Notice: Subject to any disclaimer, the term of this patent is extended or adjusted under 35 U.S.C. 154(b) by 216 days.

(21) Appl. No.: 09/679,045

(22) Filed: Oct. 4, 2000

(51) Int. Cl.⁷ .......................... B29C 43/02; G01N 11/12
(52) U.S. Cl. ....................... 425/344; 425/412; 425/416; 73/864.64
(58) Field of Search .......................... 425/78, 344, 412, 425/414, 416; 73/864.64

(56) References Cited

U.S. PATENT DOCUMENTS

| 444,887 A | 1/1891 | Menges |
| 1,078,847 A | 11/1913 | Grauenfels et al. ...... 73/864.64 |
| 1,168,486 A | 1/1916 | Des Isles ................. 73/863.31 |
| 3,080,760 A | 3/1963 | Piersma ................... 73/864.64 |
| 3,091,969 A | 6/1963 | Romanchuk et al. .... 73/863.31 |
| 3,274,303 A | 9/1966 | Müller ........................ 264/427 |
| 3,593,366 A * | 7/1971 | Smith ........................... 425/78 |
| 3,659,985 A | 5/1972 | Marshall et al. .............. 425/78 |
| 3,696,974 A | 10/1972 | Van der Veken ............ 222/251 |
| 3,775,032 A | 11/1973 | Smith et al. .................. 425/78 |
| 3,788,787 A | 1/1974 | Silbereisen et al. ........... 425/78 |
| 3,790,330 A | 2/1974 | Roland ........................ 425/412 |
| 4,061,453 A | 12/1977 | DeSantis ....................... 425/78 |
| 4,408,975 A | 10/1983 | Hack ........................... 425/345 |
| 4,411,848 A | 10/1983 | DeSantis ..................... 425/412 |
| 4,684,101 A | 8/1987 | Wagner et al. ............... 249/144 |
| 4,781,567 A | 11/1988 | Miller, Jr. .................... 425/406 |
| 4,880,373 A | 11/1989 | Balog et al. ................. 425/353 |
| 5,004,413 A | 4/1991 | Stopforth .................... 425/182 |
| 5,158,728 A | 10/1992 | Sanderson et al. .......... 425/345 |
| 5,337,620 A | 8/1994 | Kalidindi ................. 73/864.64 |
| 5,417,903 A | 5/1995 | Harrison et al. ............ 264/109 |
| 5,440,941 A | 8/1995 | Kalidindi ................. 73/864.64 |

FOREIGN PATENT DOCUMENTS

| GB | 1077122 | 7/1967 |
| JP | 60-37298 | 2/1985 |
| JP | 3-181326 | 8/1991 |
| SU | 207681 | 3/1968 |
| SU | 409789 | 5/1974 |

* cited by examiner

*Primary Examiner*—Robert Davis
*Assistant Examiner*—Thu Khanh T. Nguyen
(74) *Attorney, Agent, or Firm*—Richard C. Litman

(57) ABSTRACT

A sampling die and press for compaction of a powder sample are disclosed. The die is designed to serve both as a mold for compacting a powder sample into a tablet or caplet and as a container for sampling the powder that is to be compacted. The die is made in two pieces with the top piece of the die having a passage and the bottom piece of the die sealing the bottom opening of the passage to form a mold cavity. The invention also includes a press adapted for compacting a powder sample contained within the mold cavity of a die which serves both as a sampling container for the powder and as a mold for compaction of the powder.

8 Claims, 11 Drawing Sheets

SAMPLING DIE AND PRESS FOR COMPACTION OF POWDER SAMPLE

BACKGROUND OF THE INVENTION

1. Field of the Invention

The present invention relates to a sampling die for taking samples from a bulk powder and a press for compacting the powder in the die into a tablet or caplet form.

2. Description of The Related Art

In the pharmaceutical industry, solid pharmaceutical dosage forms such as tablets, capsules, and caplets are manufactured from a blend of active and inactive ingredients in powder form. The active and inactive ingredients are blended together in a special blender or mixer. When the blended powder is stored after blending, there is a tendency for the dry powders of the active ingredient(s) and the inactive ingredient(s) to segregate or separate, resulting in non-uniform distribution of the active ingredient(s) in the finished product. Therefore, before further processing of such blends, bulk samples are taken from different places in these blends and analyzed to check whether or not the active ingredients are uniformly distributed. Such a test is known in the trade as a content uniformity test or a homogeneity test, and requires unit-dose samples with sample sizes equal to about one dose of the product taken from different locations within the powder blend. Usually, samples of the powder blend must be transferred from the storage area to the laboratory for analysis. As a powder sample is transported some powder grains may get blown off. In addition, as the powder sample is transferred from one container to another, or from a container to a balance and vice versa, some of the powder will adhere to the container such that the sample which arrives at the laboratory for analysis may not be equivalent to a single dose as was measured when the sample was taken or immediately thereafter. To minimize this type of sampling error, the need exists in the art for an apparatus that allows the powder sample to be compacted, in the same container with which the sample was taken, into a solid tablet or caplet immediately after the sample is taken. Examples of presses for compaction of powders can be seen among the references cited below. However, none of the references cited below show a press adapted to compact powder within a die that can also serve as a sampling container. Further, none of the cited references show a die that is designed to serve both as a mold for compacting a powder sample into a tablet or caplet and as a container for sampling the powder that is to be compacted.

U.S. Pat. No. 4,411,848, issued to Raymond P. DeSantis on Oct. 25, 1983, is directed to a press for compacting powder material. The press of DeSantis uses a piston having a large diameter and a small diameter end to generate an amplified pressure in a hydraulic circuit in response to the pressure applied to a pneumatic circuit.

U.S. Pat. No. 3,274,303, issued to Werner Muller on. Sep. 20, 1966, is directed to a press for compressing a magnetizable powder to form a permanent magnet. The press of Muller has a mold or die that is open at both ends. Upper and lower punches cooperatively compress the magnetizable powder within the mold. The mold has integral magnetizing windings.

U.S. Pat. No. 4,781,567, issued to Henry A. Miller, Jr. on Nov. 1, 1988, is directed to an apparatus for evaluating the compaction properties of a medicinal powder. The apparatus of Miller uses a die that is open at both ends. A sliding anvil is used to block one end of the die and a tamping pin compresses the powder in the die from the other end of the die. The anvil has a hole that can be brought into registry with the die to eject the compressed powder.

U.S. Pat. No. 3,790,330, issued to Charles H. Roland on Feb. 5, 1974, is directed to a compaction press for compressing a powder by pressing the powder in a mold using a movable piston. The plate sealing the bottom of the mold has the plunger which is used to break up the compressed powder before repressing the powder.

U.S. Pat. No. 4,880,373, issued to Stephen Balog et al. on Nov. 14, 1989, is directed to a compaction press for compressing a powder. The press of Balog et al. uses a die which is split vertically. Also, the press of Balog et al. has both a vertical and a horizontal pressure applying means. The horizontal pressure applying means holds the die together while the vertical pressure applying means compresses the powder in the die.

U.S. Pat. No. 5,417,903, issued to Roger G. Harrison et al. on May 23, 1995, is directed to a manually operated pill press. The pill press of Harrison et al. has a storage compartment for holding a supply of powder, a blind mold cavity, and a pill ram for compressing powder within the mold cavity. The pill ram also serves to extract the formed pill from the mold cavity.

U.S. Pat. No. 3,659,985, issued to Alec Frank Marshall et al. on May 2, 1972, is directed to a press for compacting metal powders. The press of Marshall et al. has a die with a passage which extends through the entire length of the die and requires both a lower punch and an upper punch to compact a quantity of powder. U.S. Pat. No. 3,775,032, issued to Joseph E. Smith et al. on Nov. 27, 1973, also shows a powder compaction apparatus requiring both a lower punch and an upper punch. Similarly, U.S. Pat. No. 3,788,787, issued to Hermann Silbereisen et al. on Jan. 29, 1974, and U.S. Pat. No. 4,061,453, issued to Raymond P. DeSantis on Dec. 6, 1977, show further examples of powder compaction apparatuses requiring both a lower punch and an upper punch. U.S. Pat. No. 4,408,975, issued to Adolf Hack on Oct. 11, 1983, shows a tablet making press having a plurality of upper punches and lower punches.

U.S. Pat. No. 4,684,101, issued to Earl F. Wagner et al. on Aug. 4, 1987, is directed to an injection molding mold having an insert which defines in part the mold cavity and which is readily accessible for replacement from the side of the mold.

U.S. Pat. No. 5,004,413, issued to Douglas R. Stopforth on Apr. 2, 1991, shows a tablet making press having a plurality of upper punches and lower punches carried on a rotor. The rotor also carries a die plate having a die for each set of upper and lower punches. As the rotor rotates, the punches are moved by cam surfaces to compress powder in the dies into pills.

U.S. Pat. No. 5,158,728, issued to Richard Sanderson et al. on Oct. 27, 1992, shows a tablet making press for making a tablet from two distinct powder formulations. The Sanderson et al. press has a plurality of upper and lower punches which are moved in and out of dies by upper and lower cam assemblies.

Soviet Document Number 07681 by E. A. Petrov, dated Dec. 22, 1967, Soviet Document Number 409789 by the Voronezh Press Construction Bureau, dated May 21, 1974, and Japanese Published Application Number 3-181326, dated Aug. 7, 1991, all show further examples of powder compaction apparatuses requiring both a lower punch and an upper punch.

Japanese Published Application Number 60-37298 by Takeshi Katagiri, dated Feb. 26, 1985, shows a powder compaction press having a lower punch which compacts powder in a die against an upper plate which is integral with the press.

U.S. Pat. No. 444,887, issued to Carles J. Menges on Jan. 20, 1891, and United Kingdom Patent Specification Number 1,077,122 by George Ernest Alsop, dated Jul. 26, 1967, show sampling probes having an outer barrel with a penetrating tip and an opening near the penetrating tip. An inner rod is attached to a sampling receptacle located near the penetrating tip. The inner rod can be rotated to bring the opening of the sampling receptacle into or out of alignment with the opening in the outer barrel.

U.S. Pat. No. 1,078,847, issued to Wilhelm Grauenfels et al. on Nov, 18, 1913, and U.S. Pat. No. 3,080,760, issued to Henry D. Piersma on Mar. 12, 1963, show sampling probes having an outer barrel with a penetrating tip and a plurality of openings distributed along the length of the outer barrel. An inner rod has a plurality of sampling receptacles distributed along its length. The inner rod can be rotated to bring the sampling receptacles into or out of alignment with the openings in the outer barrel.

U.S. Pat. No. 1,168,486, issued to Leonard H. Des Isles on Jan. 18, 1916, shows a sampling probe having a plurality of sampling containers tied together in series by pieces of string. The first sampling container has a penetrating tip which at its base is larger in diameter than any of the sampling containers. The sampling containers are placed in an elongated tube with the penetrating tip acting as a closure for one end of the tube. A long line attached to the sampling receptacle farthest from the penetrating tip is used to keep the pieces of string between the sampling receptacles taught as the sampling probe is plunged into a bulk quantity of granular material. Once the sampling probe reaches the desired depth, then the elongated tube is removed allowing the sampling receptacles to fill with the granular material.

U.S. Pat. No. 3,091,969, issued to Steve Romanchuk et al. on Jun. 4, 1963, shows a powder metal sampling device in the form of a rectangular parallelepiped having a plurality of oblique cavities distributed along its length.

U.S. Pat. No. 3,696,974, issued to Germaine Van der Veken on Oct. 10, 1972, shows a liquid sampling device having an inner member slidably supported by an outer member. The inner member has a sampling receptacle which is exposed when the inner member is extended relative to the outer member. The sampling receptacle is closed off when the inner member is retracted relative to the outer member.

U.S. Pat. No. 5,337,620, issued to Sanyasi R. Kalidindi on Aug. 16, 1994, and U.S. Pat. No. 5,440,941, issued to Sanyasi R. Kalidindi on Aug. 15, 1995, show sampling probes having an outer barrel with a penetrating tip and an inner rod capable of holding a plurality of sampling dies. The outer barrel has a plurality of openings which expose the sampling dies when the inner rod is turned to the appropriate position relative to the outer barrel. Kalidindi '620 and Kalidindi '941 use different types of sampling dies than those disclosed herein. Further, the inner rods of Kalidindi '620 and Kalidindi '941 are not adapted to allow the removal of the sampling dies in the same manner as in the present invention.

None of the above inventions and patents, taken either singularly or in combination, is seen to describe the instant invention as claimed. Therefore, the need persists for a sampling die which can also serve as a molding die for compacting a powder and for a press for compacting the powder sample contained within such a sampling die.

SUMMARY OF THE INVENTION

The present invention is directed to a die that is designed to serve both as a mold for compacting a powder sample into a tablet or caplet and as a container for sampling the powder that is to be compacted. The die is made in two pieces. The top piece of the die has a passage extending through the thickness of the top piece. The bottom piece of the die acts as a removable closure for the bottom opening of the passage in the top piece in order to form a mold cavity. The present invention also includes a press adapted for compacting a powder sample contained within the mold cavity of a die which serves both as a sampling container for the powder and as a mold for compaction of the powder.

Accordingly, it is a principal object of the invention to provide a die which serves both as a sampling container for a powder and as a mold for compaction of the powder.

It is another object of the invention to provide a die which can serve as a mold for the compaction of a powder sample and which is adapted to fit into a sampling probe designed for insertion into a bulk powder.

It is a further object of the invention to provide a two-piece die having a bottom piece which can be removed to allow the ejection of the final product from the die.

Still another object of the invention is to provide a press adapted for compacting a powder sample contained within the mold cavity of a die which serves both as a sampling container for the powder and as a mold for compaction of the powder.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

DESCRIPTION OF THE DRAWINGS

Similar reference characters denote corresponding features consistently throughout the attached drawings.

DETAILED DESCRIPTION OF THE PREFERRED EMBODIMENTS

Figure 1:
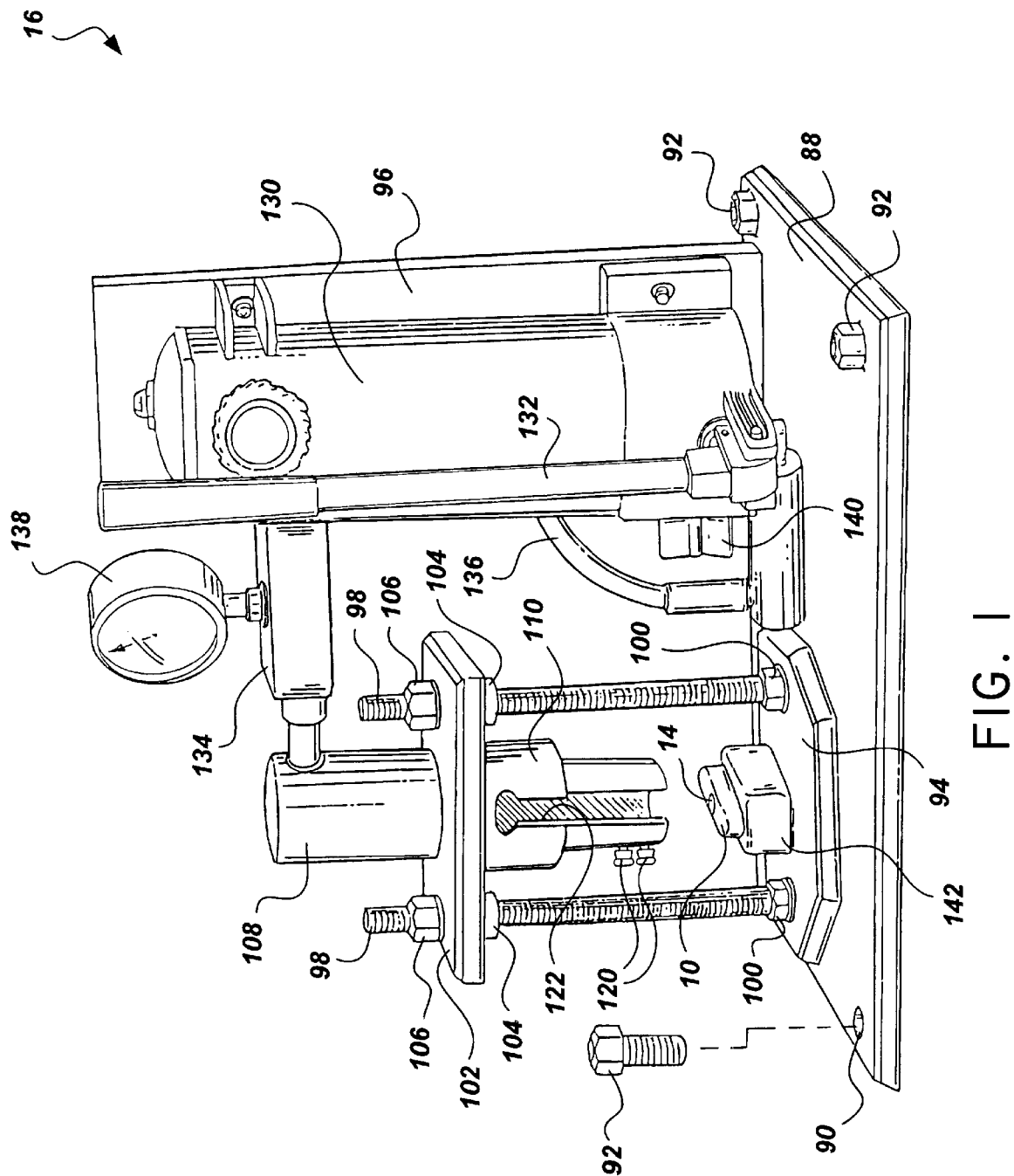
FIG. 1 is a perspective view of a pharmaceutical press adapted to compact powder within a die that can also serve as a sampling container, according to the present invention.

Referring to FIGS. 1 and 5–10, the present invention is directed to sampling dies 10, 10a, and 10b that are adapted for placement in a sampling probe 12. When the sampling probe 12 is inserted in a bulk powder product, the die 10, 10a, or 10b is directly filled with a quantity of powder which is determined by the size of the die cavity 14 or 14a. The invention also includes a powder compaction press 16 which is adapted for compressing the powder sample within the sampling die 10, 10a, or 10b into a tablet or caplet, while the powder sample remains in the sampling die during the compaction process. Thus, in addition to being the container in which the powder sample is taken, the sampling die 10, 10a, or 10b also serves as the molding die for forming the tablet or caplet.

Figure 6:
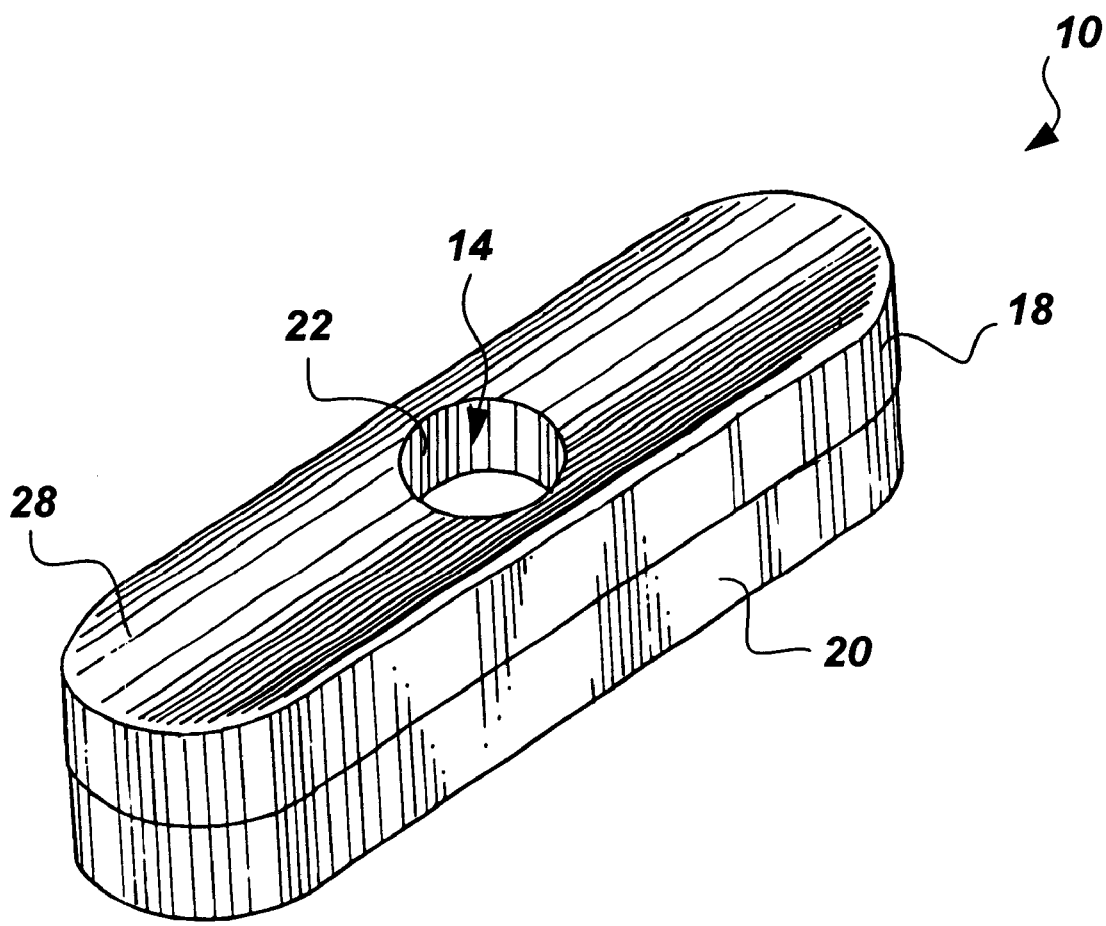
FIG. 6 is a top perspective view of a die for making round tablets according to the present invention.
Figure 7:
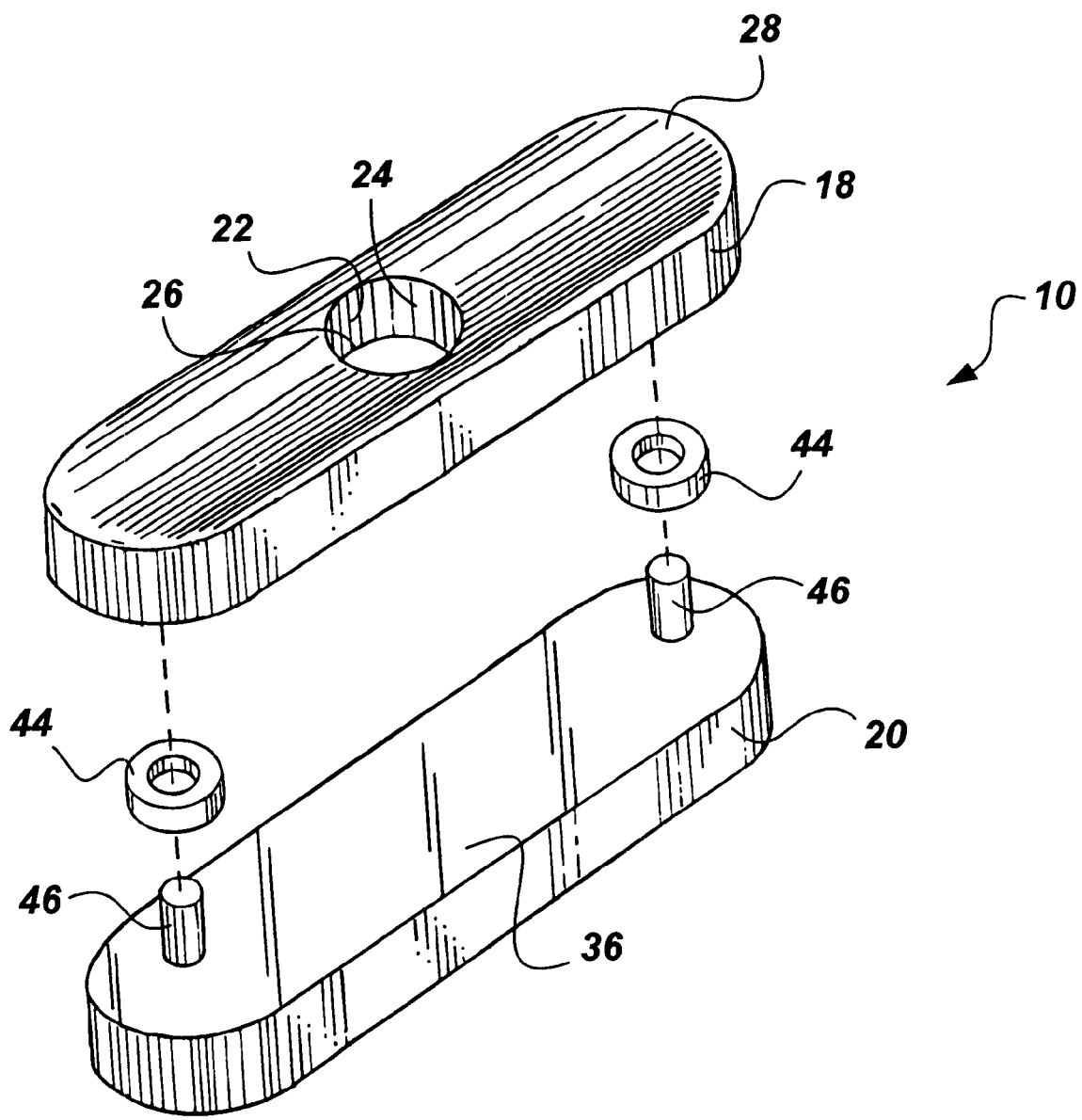
FIG. 7 is an exploded top perspective view of a die for making round tablets according to the present invention.
Figure 8:
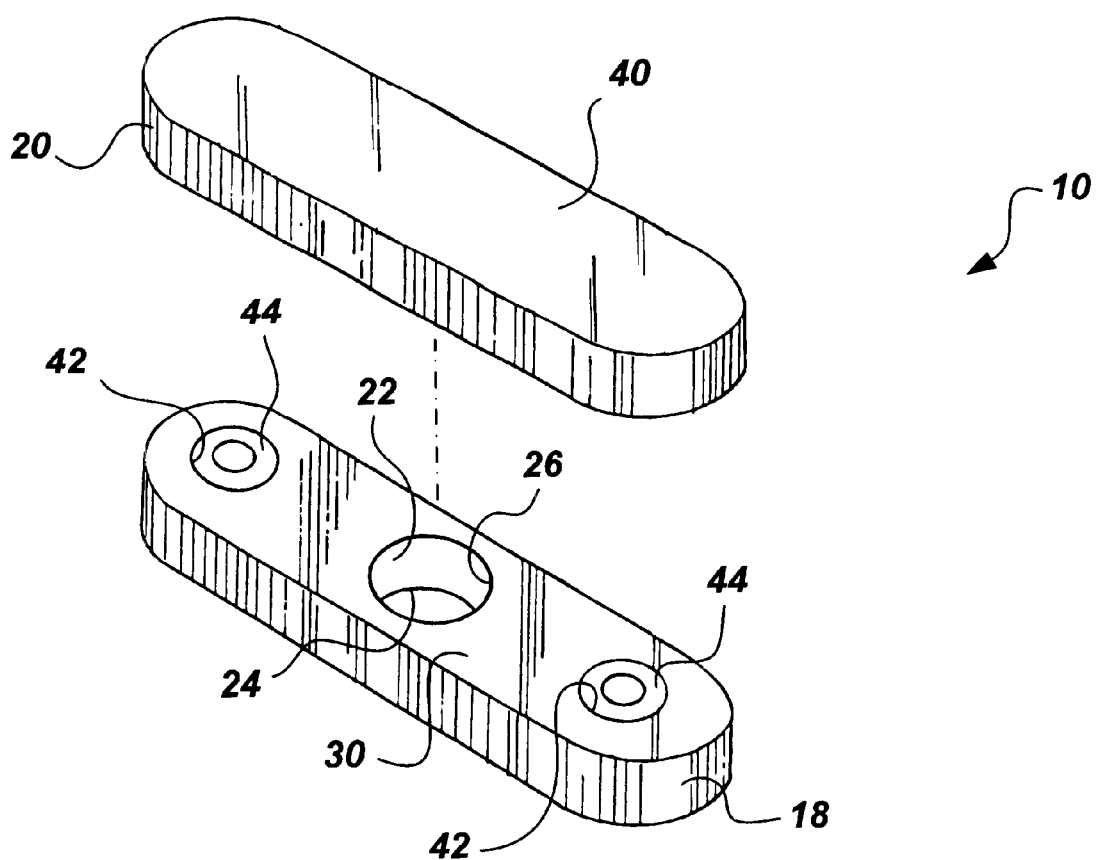
FIG. 8 is an exploded bottom perspective view of a die for making round tablets according to the present invention.

Referring to FIGS. 6–8, the powder sampling and compaction die 10 includes a top piece 18 and a bottom piece 20. The top piece 18 has a passage 22 which extends completely through the thickness of the top piece 18. The passage 22 has a top opening 24 and a bottom opening 26. The die 10 has a top surface 28 and a bottom surface 30. The top surface 28 of the top piece 18 has a contour which follows a portion of a cylindrical surface of an imaginary cylinder having a longitudinal axis which runs parallel to the lengthwise direction of the die 10. More specifically, the imaginary cylinder is the cylinder defined by the exterior surface 32 of the die holder tube 34 of the sampling probe 12. The bottom surface 30 of the top piece 18 abuttingly contacts the top surface 36 of the bottom piece 20 when the top piece 18 and the bottom piece 20 are assembled together. The top opening 24 is defined by the passage 22 intersecting the top surface 28 of the top piece 18, and the bottom opening 26 is defined by the passage 22 intersecting the bottom surface 30 of the top piece 18.

The top piece 18 has an outline which is elongated and has rounded ends when the top piece 18 is viewed in plan view. The bottom piece 20 has a substantially identical outline in plan view as compared to the top piece 18, such that the outline of the top piece 18 is superimposed upon the outline of the bottom piece 20 when the top piece and the bottom piece are assembled together. With the top piece 18 and the bottom piece 20 assembled together, the die 10 is shaped and sized to fit in one of the cavities 38 of the die holder tube 34.

When the top piece 18 and the bottom piece 20 are assembled together, the bottom surface 30 of the top piece 18 abuttingly contacts the top surface 36 of the bottom piece 20 such that the passage 22 and the top surface 36 of the bottom piece 20 cooperatively form the mold cavity 14. The bottom piece 20 has a substantially flat bottom surface 40 in to allow the die 10 to be stably supported when the die 10 is positioned in the press 16.

The dies 10, 10a, and 10b include means for releasably securing the bottom piece of the die to the top piece of the die. In the example illustrated in FIGS. 6–8, the securing means is formed by a pair of holes 42 formed in the bottom surface 30 of the top piece 18, a pair of rubber bushings 44, and a pair of pegs 46. The pair of holes 42 open to the bottom surface 30 of the top piece 18. Each of the pair of rubber bushings 44 is inserted in a respective one of the pair of holes 42. Each of the pair of rubber bushings 44 is sized such that it is in a friction fit within the respective one of the pair of holes 42. The pair of pegs 46 project from the top surface 36 of the bottom piece 20. The pair of pegs 46 are positioned on the surface 36 such that each of the pegs 46 is received within a respective one of the pair of rubber bushings 44 in a friction fit with the respective rubber bushing. When the top piece 18 and the bottom piece 20 are assembled together, the rubber bushings 44 will frictionally engage the bore of the holes 42 and the pegs 46 to thereby releasably secure the top piece 18 and the bottom piece 20 together.

The top opening 24 of the passage 22 is sized to allow the tip of the punch 48 (see FIG. 2) to pass through the top opening 24 and project into the passage 22. To form a tablet, the mold cavity 14 is filled with a quantity of powder, as will be described later, and the quantity of powder is then formed into a tablet by compacting the quantity of powder within the mold cavity 14 using the punch 48. The passage 22 preferably has a uniform cross sectional area in plan view such that the punch 48 can be used to eject the tablet, formed by compacting the powder in the mold cavity 14, from the passage 22 after the bottom piece 20 is removed from the top piece 18. In the die 10, the passage 22 is substantially circular in plan view such that the quantity of powder, placed in the mold cavity 14, forms a tablet which is substantially circular in plan view after the quantity of powder is compacted in the mold cavity.

Figure 9:
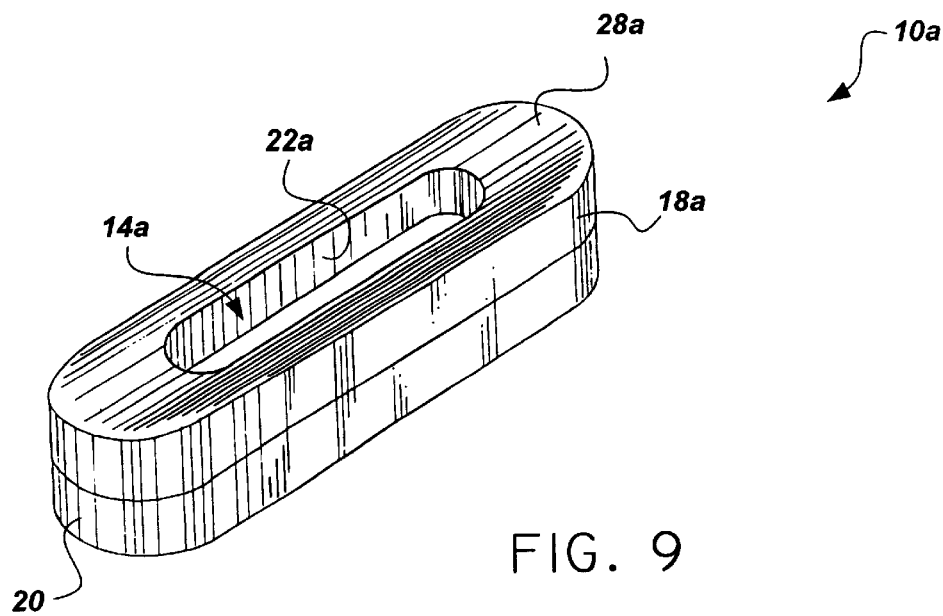
FIG. 9 is a top perspective view of a die for making caplets according to the present invention.

Referring to FIG. 9, the die 10a is identical to the die 10 in all respects, except that the passage 22a of the top piece 18a is elongated and has rounded ends in plan view. Therefore, the molding cavity 14a, formed cooperatively by the passage 22a and the top surface of the bottom piece 20, will also have an outline in plan view which is elongated and has rounded ends. Because the powder compacted in the molding cavity 14a will assume the shape of the molding cavity, the product formed by compacting powder in the mold cavity 14a will be elongated in shape and will somewhat resemble a capsule. Products formed by the compaction of powder and having this elongated shape are known in the pharmaceutical industry as caplets. As with the top piece 18, the top surface 28a of the top piece 18a follows the curvature of an imaginary cylindrical surface defined by the exterior surface of the die holder tube 34 of the sampling probe 12.

Figure 10:
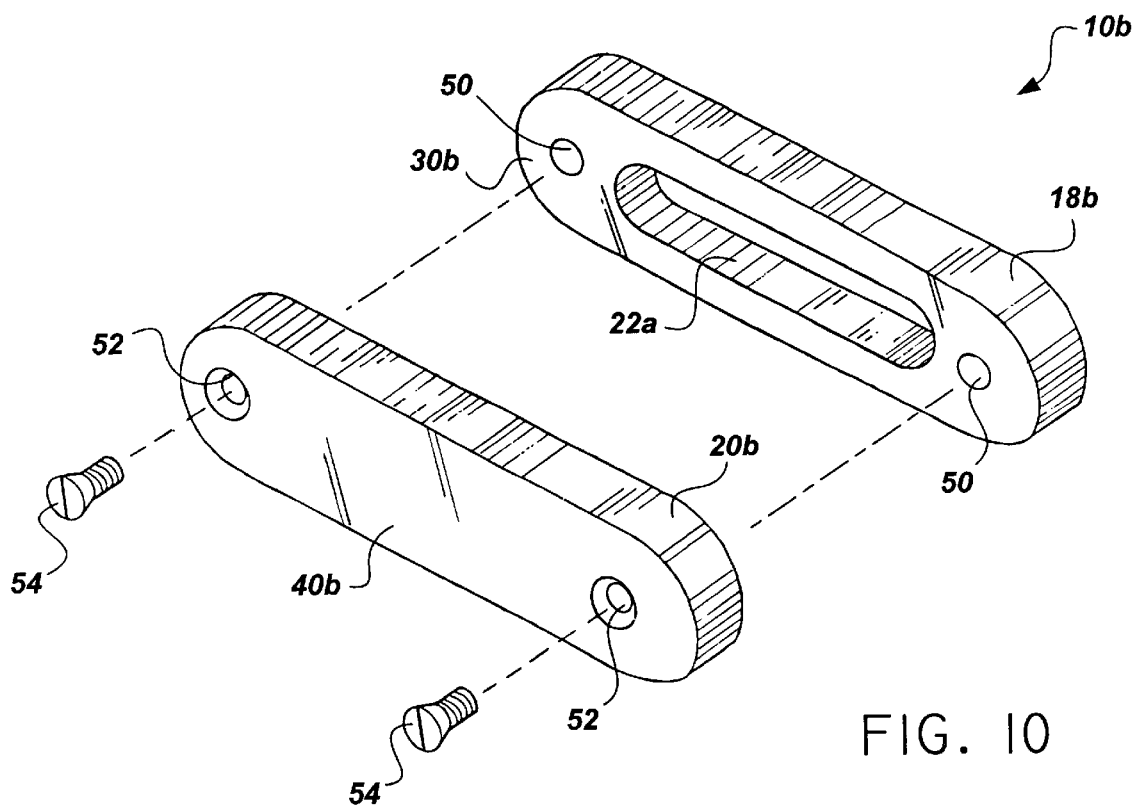
FIG. 10 is an exploded bottom perspective view of a die for making caplets according to the present invention, with the die using an alternative means for securing the two pieces of the die together.
Figure 11:
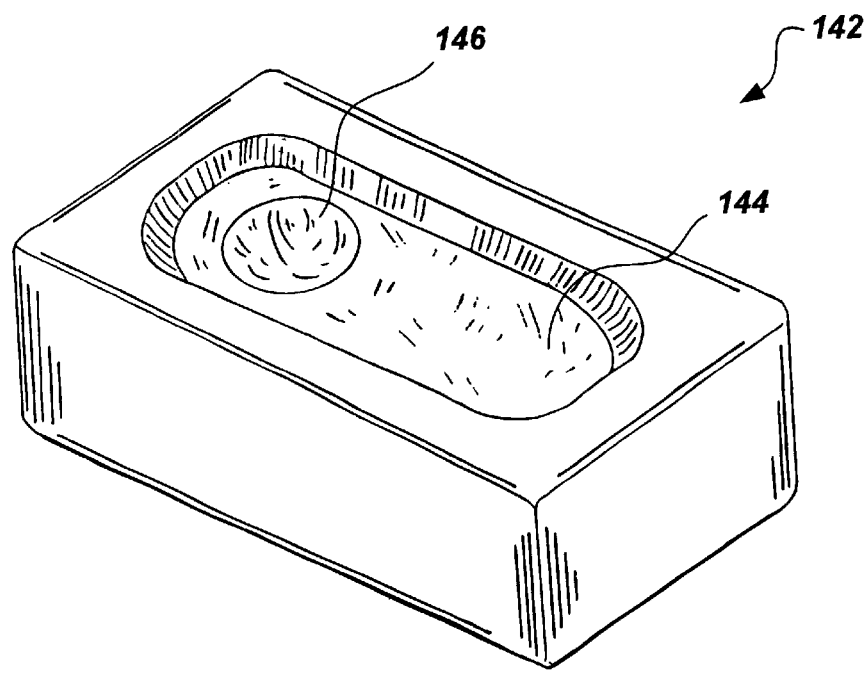
FIG. 11 is a top perspective view of die support adapted for use with the die and press of the present invention.

Referring to FIG. 10, the die 10b is identical to the die 10a in all respects, except that an alternative means is used in the die 10b to releasably secure the bottom piece 20b to the top piece 18b. The top piece 18b has a first pair of holes 50 which are threaded. Each of the holes 50 opens to the bottom surface 30b of the top piece 18b. The bottom piece 20b has a second pair of holes 52 which extend from the bottom surface 40b of the bottom piece 20b to the top surface of the bottom piece 20b. Each of the holes 52 is in registry with a respective one of the holes 50 when the top piece 18b and the bottom piece 20b are assembled together. Each of a pair of screws 54 extending through a respective one of the holes 52 and threadedly engages a respective one of the holes 50 to; thereby releasably secure the bottom piece 20b to the top piece 18b. Preferably, the holes 52 are counter-sunk adjacent the surface 40b and the screws 54 are flat head screws such that the heads of the screws 54 will not disturb the stable support afforded to the die 10b by the substantially flat bottom surface 40b.

It should be readily apparent that the size and shape of the passage (e.g. 22 and 22a) through the top piece of the die can be varied independently of the means used to secure the top piece of the die to the bottom piece of the die. Thus, a top piece having a passage with the shape of either the passage 22 or the passage 22a, can be combined with either of the means for releasably securing the bottom piece to the top piece as disclosed herein without departing from the scope of the present invention. Furthermore, the passages 22 and 22a can have cross sectional areas of any desired shape and size so long as a punch with a matching tip shape is used to compact the powder within the sampling die.

Figure 5:
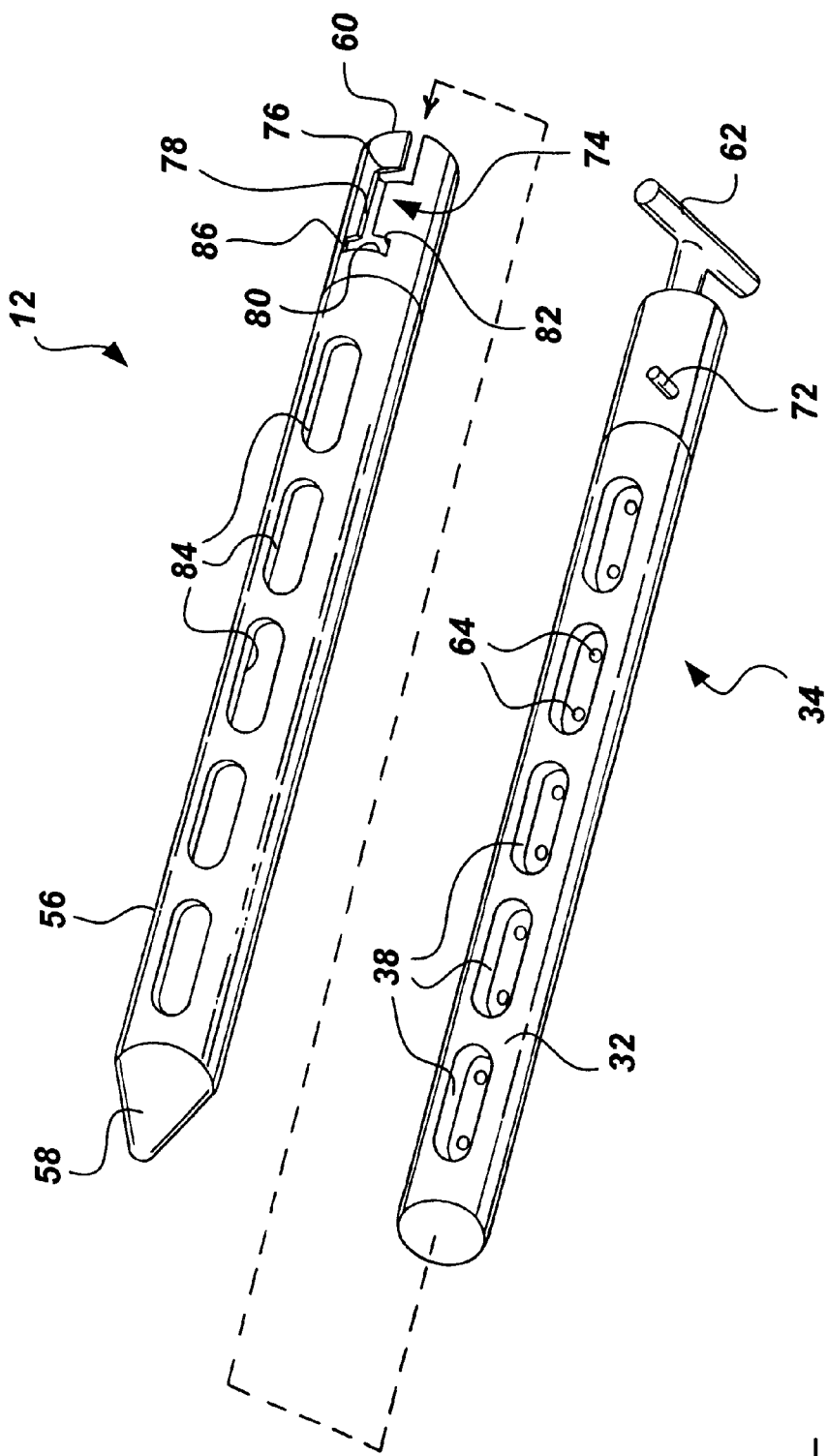
FIG. 5 is an exploded view of a pharmaceutical powder sampler adapted for use with the die and press of the present invention.

The powder compaction press 16 and the sampling dies 10, 10a, and 10b are particularly well suited for use as part of a system which includes the sampling probe 12 shown in FIG. 5. The sampling probe 12 includes an outer tube 56 having a substantially conical first end 58 and an open second end 60. The sampling probe 12 also includes a die holder tube 34 which snugly fits in the bore of the outer tube 56. Attached to the die holder tube 34 is a T-shaped handle 62 which remains outside the bore of the outer tube 56 when the die holder tube 34 is inserted into the bore of the outer tube 56 to its fullest extent. The die holder tube 34 has a plurality of cavities 38 distributed along its length. Each of the cavities is adapted for receiving a sampling die such as the dies 10, 10a, and 10b. The depth of the cavities 38 is selected such that when any of the fully assembled dies 10, 10a, and 10b is placed in a cavity 38, the top surface 28 or 28a of the die will be flush and contiguous with the exterior surface 32 of the die holder tube 34.

Figure 12:
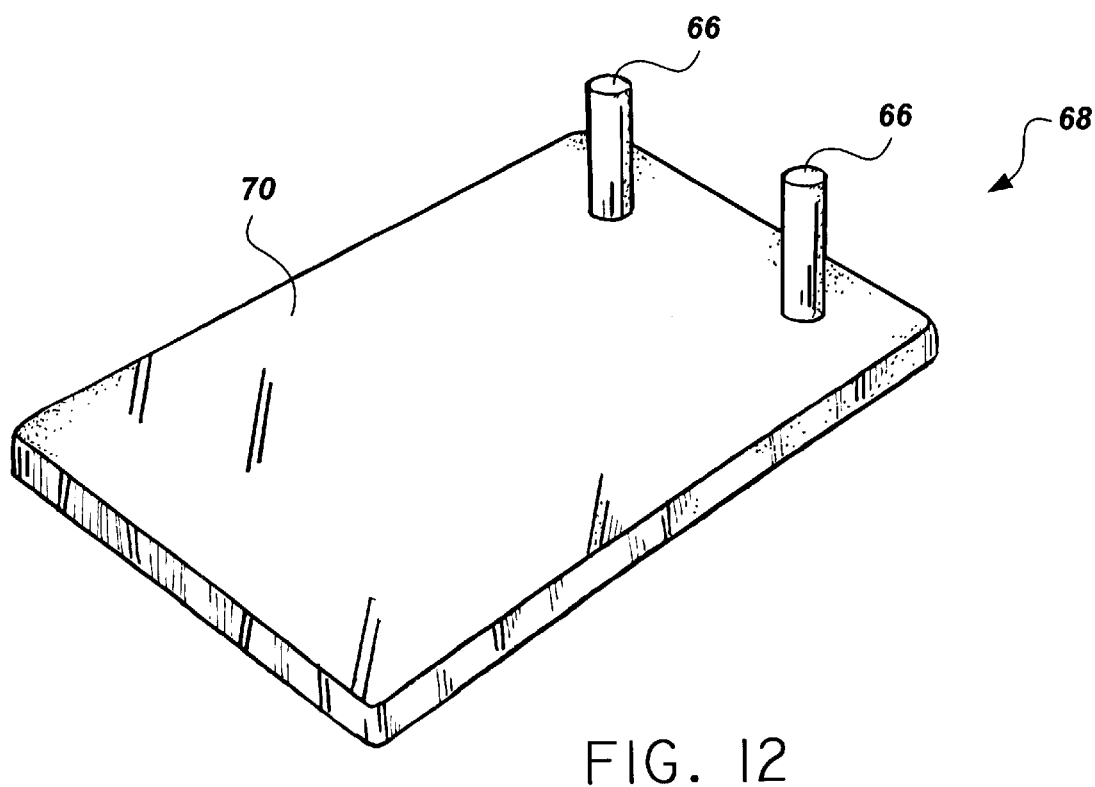
FIG. 12 is a top perspective view of a tool adapted for removing a die made according to the present invention from a sampling probe.
Figure 13:
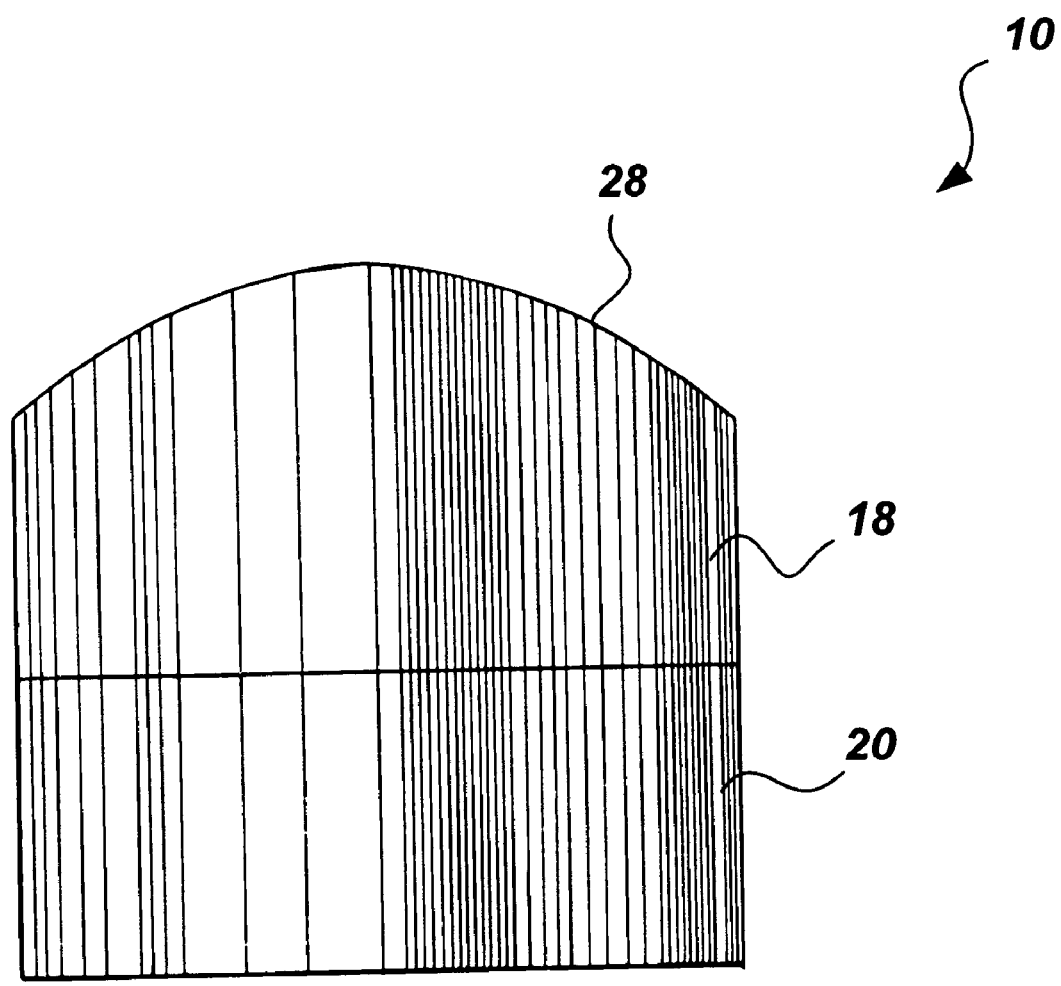
FIG. 13 is a view of a sampling die according to the present invention, shown in elevation to illustrate the curvature of the top surface of the die.

Each cavity 38 has a pair of holes 64 to allow the prongs 66 of the die removal tool 68 to be used to dislodge a sampling die from a cavity 38 (see FIG. 12). Each hole 64 extends from the bottom of a cavity 38 to the other side of the die holder tube 34, coaxial with a diameter of the die holder tube 34. The die removal tool 68 includes a rectangular plate 70. The prongs 66 project perpendicularly from the same side of the plate 70. The prongs 66 are positioned near one end of the plate 70. The center-to-center distance of the prongs 66 is essentially the same as the center-to-center distance of the pair of holes 64 that open to the bottom of a given cavity 38, such that the prongs 66 can be simultaneously inserted through a pair of holes 64 corresponding to a given cavity 38 from the bottom in order to partially raise a die 10, 10a, or lob out of the cavity 38. Each pair of holes 64 may be replaced by an elongated slot without departing from the spirit and scope of the present invention.

In use, a plurality of dies 10, 10a, or lob are placed in the cavities 38, one die being placed in each cavity. The die holder tube 34 is then inserted into the outer tube 56 with the guide peg 72 aligned with the open mouth of the guide slot 74. Progress of the die holder tube 34 is stopped when the peg 72 contacts the first transverse portion 76 of the guide slot 74. The handle 62 is then turned clockwise until the peg 72 is aligned with the second axial portion 78. The insertion of the die holder tube 34 into the outer tube 56 is then continued until the peg 72 contacts the bottom edge of the second transverse portion 80. The handle 62 is then turned clockwise until the peg 72 contacts the end 86 of the second transverse portion of the guide slot 74. With the guide peg 72 in contact with the end 86 of the second transverse portion of the guide slot 74, the cavities 38 will be rotated out of alignment with the openings 84 and the mold cavities 14 or 14a will be closed off so that the mold cavities 14 or 14a will not fill with powder before the sampling dies 10, 10a, or 10b have reached the desired locations within a quantity of bulk pharmaceutical powder.

While the sampling probe 12 is in the configuration described above, the sampling probe is plunged into a quantity of bulk pharmaceutical powder to a user selected depth such that the sampling dies 10, 10a, or 10b will be positioned at desired locations within the bulk pharmaceutical powder. The handle 62 is then turned counter clockwise until the peg 72 contacts the end 82 of the second transverse portion 80. With the peg 72 in contact with the end 82 of the second transverse portion 80, each of the cavities 38, and thus each of the dies 10, 10a, or 10b, will be in registry with a respective one of the openings 84 which extend through the wall of the outer tube 56. Thus, the mold cavities 14 or 14a of the dies 10, 10a, or 10b will be exposed when the peg 72 is in contact with the end 82 of the second transverse portion 80 of the guide slot 74. The pharmaceutical powder will then fill the mold cavities 14 or 14a which are positioned below the level of the bulk pharmaceutical powder. Once the mold cavities of the desired dies 10, 10a, or 10b are filled with powder, the handle 62 is turned clockwise until the peg 72 contacts the end 86 of the second transverse portion of the guide slot 74. With the guide peg 72 in contact with the end 86 of the second transverse portion of the guide slot 74, the cavities 38 will be rotated out of alignment with the openings 84 and the mold cavities 14 or 14a will be closed off such that the powder sample contained in the mold cavities cannot spill out of the mold cavities as the sampling probe 12 is withdrawn from the bulk powder.

Once the sampling probe 12 is withdrawn from the bulk powder, the sampling probe 12 is placed on a rack (not shown) such that the longitudinal axis of the probe is horizontal. With the openings 84 facing upward, the handle 62 is turned counter clockwise to align the guide peg 72 with the second axial portion 78 of the guide slot 74. Pulling the handle 62 outward relative to the outer tube 56, results in the guide peg 72 moving along the second axial portion 78 of the guide slot 74 until the guide peg 72 reaches the first transverse portion 76 of the guide slot 74. The handle 62 is again turned counter clockwise to align the guide peg 72 with the open mouth of the guide slot 74. With the guide peg 72 aligned with the open mouth of the guide slot 74, the guide peg 72 is also aligned with the position the guide peg 72 occupied when the guide peg was in contact with the end 82 of the second transverse portion of the guide slot 74. The die holder tube 34 can now be completely removed from the outer tube 56 while the dies in the cavities 38 remain in an upward facing orientation. Thus, the die holder tube 34 can be removed from the outer tube 56 without any of the powder samples in any of the mold cavities 14 or 14=abeing spilled.

The die holder tube 34 is then placed on a rack (not shown) while the tube's longitudinal axis remains in a horizontal orientation. Also, the die holder tube 34 is maintained in an orientation such that the dies 10, 10a, or 10b are maintained in an upward facing orientation at all times so as to prevent any of the powder samples contained in the dies from spilling. The die removal tool 68 can then be used to remove each of the dies 10, 10a, or 10b from its respective cavity 38. Once each die is removed from the die holder tube 34, the die can be transferred to the powder compaction press 16 where the powder sample in the die 10, 10a, or 10b can be compacted into a tablet or caplet of the desired hardness.

Referring to FIGS. 1–4 and 11, the construction and operation of the powder compaction press 16 will be explained. The press 16 includes a base plate 88 which has four holes 90. The holes 90 allow the base plate 88 to be bolted to a bench top or a cart using the bolts 92, so as to provide a stable support for the press 16. The base plate 88 may include an optional platform 94 which is fixed to the top side of the base plate 88. The platform 94 is located on one side of the midline of the base plate 88. A pump support plate 96 is also fixed to the top side of the base plate 88. The pump support plate 96 projects perpendicularly from the top side of the base plate 88, and the pump support plate 96 is located on the side of the midline of the base plate 88 opposite the side on which the platform 94 is located.

A pair of threaded shafts 98 extend perpendicularly from the top surface of the base plate 88 and through the platform 94. The lower end of each shaft 98 is received in a threaded hole in the base plate 88. The nuts 100 lock and secure the shafts 98 in place. A punch holder support plate 102 is supported by the shafts 98 above the top surface of the platform 94. The punch holder support plate 102 has clearance holes for the shafts 98. Threaded collars 104 hold the punch holder support plate 102 up along the shafts 98. Threaded collars 104 are secured in place using set screws (not shown). The set screws threadedly engage passages which extend radially through each collar 104. When the set screws are tightened, they frictionally engage the shafts 98 to lock the collars 104 in place.

The nuts 106 are tightened down on the punch holder support plate in order to prevent the punch holder support plate 102 from being lifted as the punch 48 is used to compact the powder placed in the mold cavity 14 of the die 10. For illustrative purposes the press 16 is shown in FIG. 1 while being used in conjunction with the die 10, however, the press 16 can be used with any of the dies 10, 10a, and 10b as long as a matching punch is used.

A piston housing 108 is fixed to the punch holder support plate 102. The piston housing 108 is positioned to extend above the punch holder support plate 102. Also fixed to the punch holder support plate 102, is a punch holder 110. The punch holder 110 extends below the punch holder support plate 102. The punch holder 110 has a central passage 112 which has a first portion 114 and a second portion 116. The piston 118 is slidably supported by the piston housing 108 and the piston 118 is axially aligned with the central passage 112. The first portion 114 of the central passage 112 has a larger diameter than the second portion 116 of the passage 112. Two thumb screws 120 threadedly engage passages extending through the wall of the punch holder 110 at a location along the second portion 116 of the passage 112. A T-shaped slot 122 is cut in one side of the punch holder 110.

The punch 48 has a head 124, a shaft 126, and a tip 128. The largest outside diameter of the shaft 126 is selected such that the punch shaft 126 can fit inside the second portion 116 of the passage 112 with just enough clearance to allow slidable movement of the punch 48 within the passage 112. The outside diameter of the punch head 124 is larger than the inside diameter of the second portion 116 of the passage 112, but the outside diameter of the punch head 124 is small enough to fit inside the first portion 114 of the central passage 112 without interfering with the movement of the punch 48 along the central axis of the passage 112. Thus, the length of the first portion 114 of the central passage 112 will define the limits of the axial movement of the punch 48.

Figure 2:
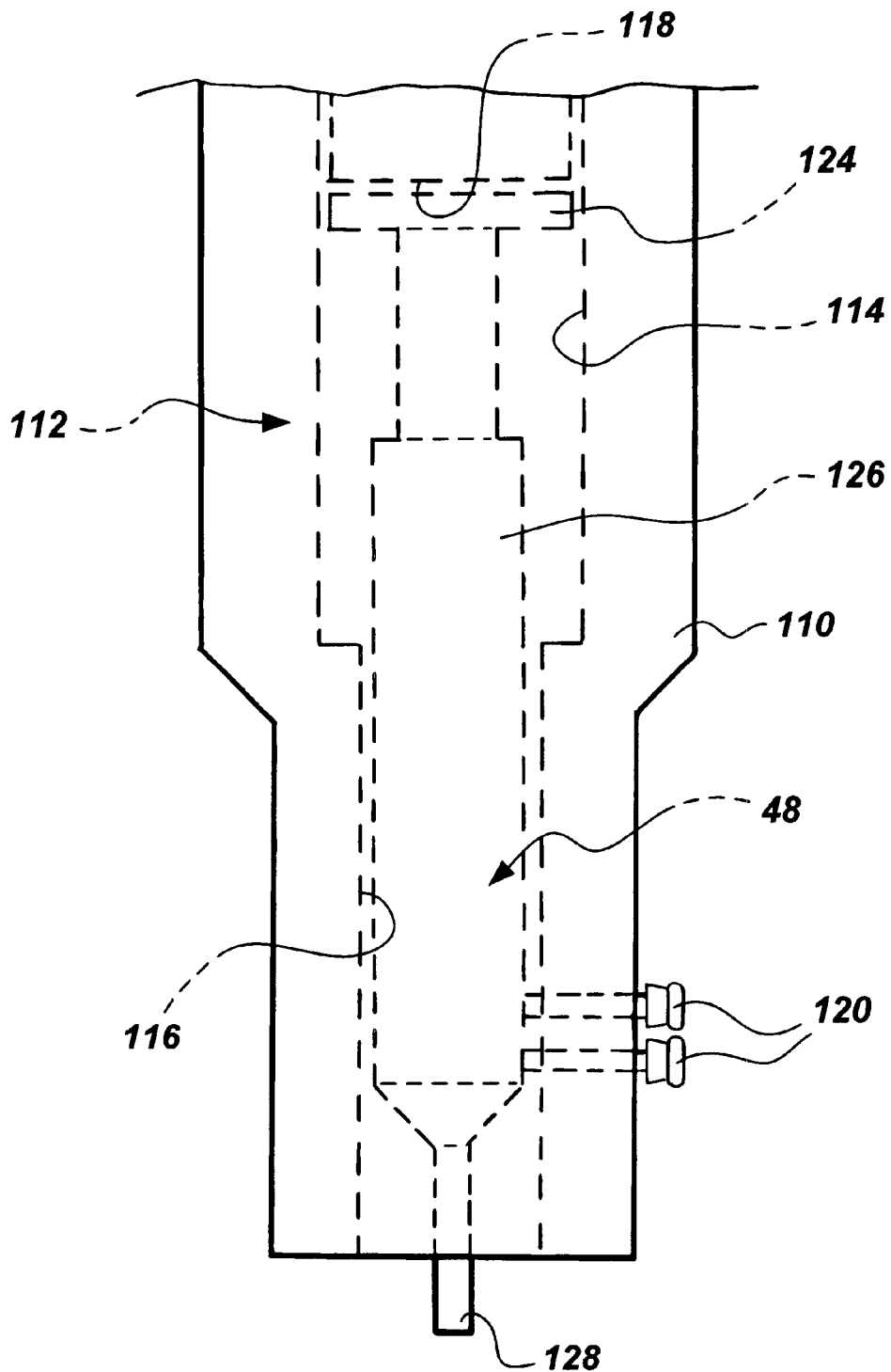
FIG. 2 is a fragmentary view of the punch holder of a pharmaceutical press adapted to compact powder within a die that can also serve as a sampling container, according to the present invention.
Figure 3:
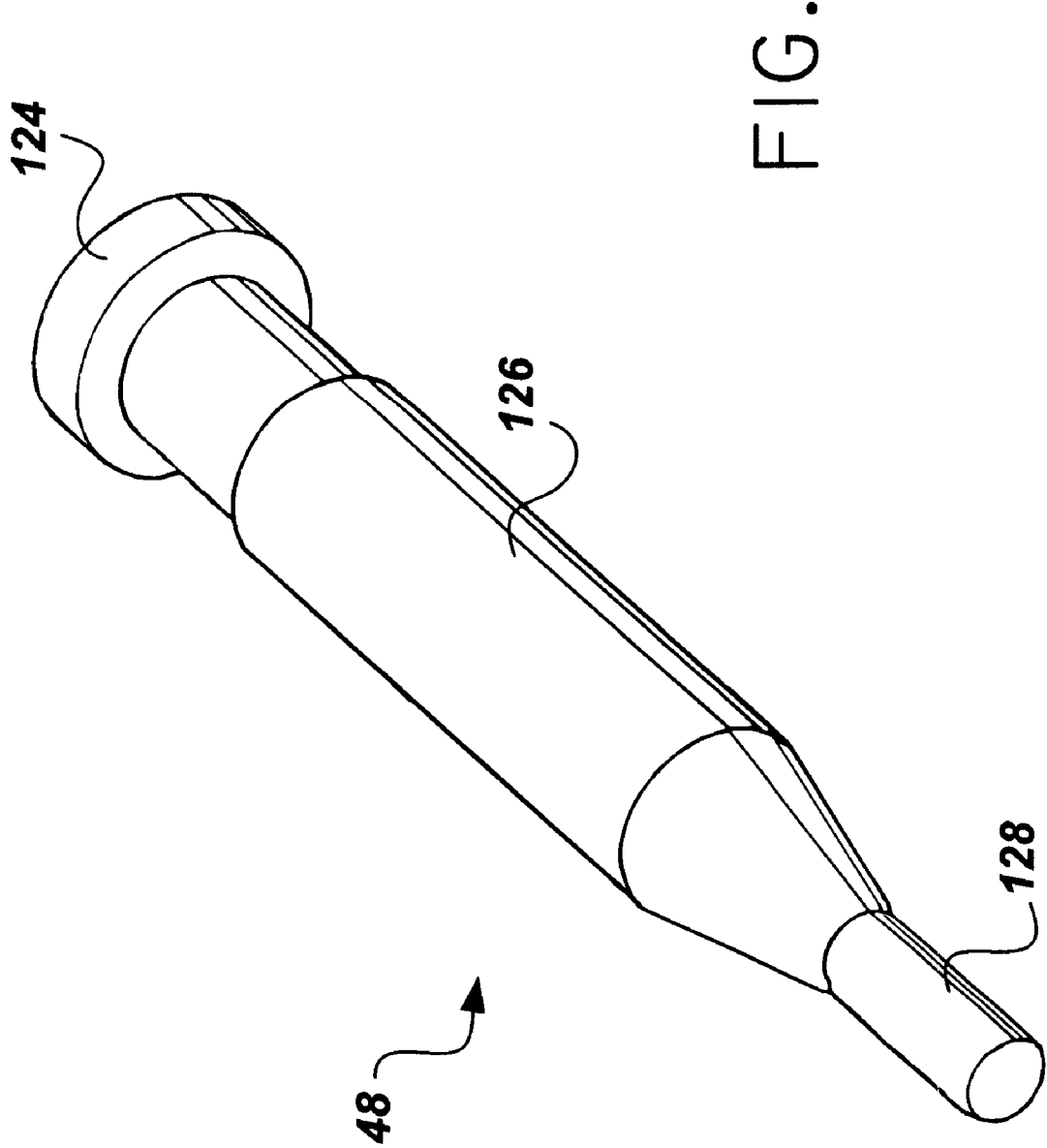
FIG. 3 is a perspective view of a punch for making round tablets according to the present invention.

The T-shaped slot 122 allows the punch 48 to be inserted into the passage 112 from one side of the punch holder 110. Once the punch 48 is placed inside the passage 112, the punch head 124 will be in registry with the piston 118 as shown in FIG. 2. The piston 118 is smaller in diameter than the first portion 114 of the central passage 112. Once the punch 48 is placed inside the passage 112 with the punch head 124 in contact with the piston 118, then the piston 118 can be used to urge the punch 48 downward toward the base plate 88.

When the punch 48 is pushed upward within the punch holder 110 as far as the punch and the piston 118 can go, then the punch 48 will be in its fully retracted position. The thumb screws 120 are used to hold the punch 48 in continuous contact with the piston 118. As the thumbscrews 120 are turned to move inward into their respective threaded passages, the thumb screws will eventually penetrate into the second portion 116 of the passage 112 and will contact the shaft of the punch 48. With the punch 48 in the retracted position, the thumb screws 120 are tightened to exert just enough frictional force on the punch 48 to prevent the punch 48 from falling away from the piston 118 due to the gravitational force exerted on the punch 48. When the punch head 124 encounters the constriction in the passage 112, the downward progress of the punch 48 will be stopped and the punch 48 will be in its fully extended position.

The punch tip 128 is adapted to fit into the passage 22 of the die 10. When a pressurized fluid is applied to the volume enclosed by the piston housing 108 and the piston 118, the piston 118 and consequently the punch 48 can be forcefully urged downward to compact the powder contained in the mold cavity of the die 10.

In the illustrated example, the means for supplying a pressurized fluid to the piston housing 108 includes a hydraulic pump 130 which is actuated by the lever 132. The hydraulic pump 130 is fixed to the pump support plate 96. The outlet of the pump 130 is in communication with the tubing fixture 134 via the flexible pressure hose 136. In turn, the tubing fixture 134 is in communication with the volume enclosed by the piston housing 108 and the piston 118. In addition, the tubing fixture 134 supports a pressure gauge 138 which shows the pressure being applied to the piston 118 by the hydraulic fluid in the piston housing 108. The internal construction of the pump 130 is well known and therefore is not discussed in detail here. The hydraulic pump 130 has an internal reservoir of hydraulic fluid. By manually pivoting the lever 132 back and forth, the hydraulic fluid is pressurized and supplied to the piston housing 108 to thus urge the piston 118 forcefully downward. Opening the pressure relief valve 140 relieves the hydraulic pressure on the piston 118 and allows the punch 48 to be manually moved back to its retracted position. The pump 130 allows pressures of up to 4000 lbs. to applied to the piston 118.

A die support block 142 is used to support the die 10, 10a, or 10b under the punch holder 110. One side of the die support block 142 is flat and is used to support the fully assembled die during the powder compaction process. The other side of the die support block 142 has a first elongated depression 144. Inside the depression 144 is an even deeper depression 146. The depression 146 is located to one side of the depression 144. The side of the block 142 having the depression 144 is used to support the top piece of the die 10, 10a, or 10b after the compaction process when the fully formed tablet or caplet is being ejected out of the top piece of the die.

Figure 4:
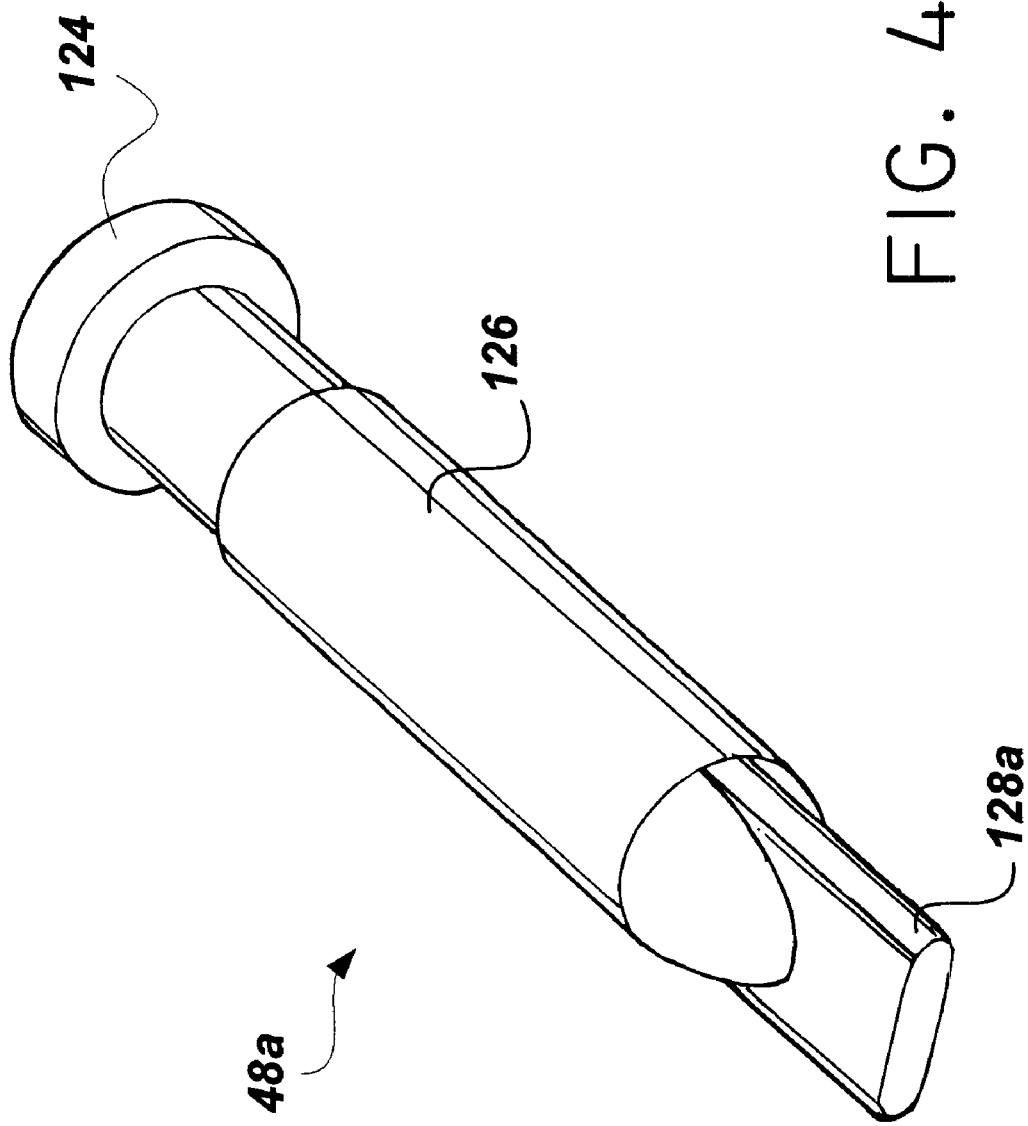
FIG. 4 is a perspective view of a punch for making caplets according to the present invention.

Referring to FIG. 4, a punch 48a for making caplets can be seen. The punch 48a is identical to the punch 48 except for the tip 128a of the punch 48a being different from the tip 128 of the punch 48. The tip 128a is sized and shaped to fit the passage 22a of the top pieces 18a and 18b of the dies 10a and 10b, respectively. Compacting the powder in the mold cavity 14a using the punch 48a results in the formation of an elongated caplet.

To use the press 16, the relief valve 140 must first be opened and the piston 118 must be pushed up as far as it will go. Then a punch 48 or 48a is placed in the punch holder 110 through the slot 122 and manually pushed to its fully retracted position. The thumb screws 120 are then used to retain the punch in the fully retracted position. The relief valve 140 can then be closed. Next, the block 142 is placed below the punch holder 110 with the flat side thereof facing up. The die 10, 10*a*, or 10*b* containing the powder sample is then placed on the block 142 with the mold cavity 14 or 14*a* in registry with the respective punch tip 128 or 128*a*. The pump handle 132 is then manually pivoted back and forth to urge the punch tip into the mold cavity. The pivoting of the handle back and forth is continued until the pressure gauge 138 indicates that the pressure corresponding to the desired hardness in the final tablet or caplet product has been reached. The back and forth pivoting of the handle 132 is then stopped and the relief valve 140 is opened. The punch is then manually returned to the fully retracted position. The die is then removed and disassembled and the block 142 is turned over such that the depression 146 faces the punch holder 110. The top piece of the die is then placed transversely over the depression 144 such that the passage 22 or 22*a* is positioned over the depression 146. The block 142 moved to bring the passage 22 or 22*a* into registry with the punch head 128 or 128*a*, respectively. Once again the pump handle 132 is manually pivoted back and forth to urge the punch tip into the passage 22 or 22*a* in order to push the completed tablet or caplet out of the passage 22 or 22*a*. The completed tablet or caplet will then fall into the depression 146 and can be retrieved by the user after the punch is retracted and the block 142 is removed from the press 16.

The completed tablet or caplet can then be analyzed to determine if it contains the proper proportion of active ingredients. In each particular sampling project the die, the punch, and the compaction pressure are selected to duplicate as nearly as possible the conditions used to manufacture the commercial tablet or caplet product. This practice provides the most accurate indicator of the expected variability in the proportion of active ingredients, on a tablet to tablet or caplet to caplet basis, in a commercial tablet or caplet product that is to be made from a given batch of bulk pharmaceutical powder.

It is to be understood that the present invention is not limited to the embodiments described above, but encompasses any and all embodiments within the scope of the following claims.

I claim:

1. A powder sampling and compaction die comprising:
    a top piece having a thickness and a passage extending through said thickness, said passage having a top opening and a bottom opening, at least said top opening being adapted for allowing at least a portion of a punch to pass through said top opening and project into said passage;
    a bottom piece having a top surface and a bottom surface; and
    means for releasably securing said bottom piece to said top piece such that said passage and said top surface of said bottom piece cooperatively form a mold cavity;
    wherein said top piece has an outline which is elongated and has rounded ends when said top piece is viewed in plan view, said bottom piece has a substantially identical outline in plan view as compared to said top piece, said outline of said top piece is superimposed upon said outline of said bottom piece when said top piece and said bottom piece are assembled together, and said top piece and said bottom piece are adapted to fit in a sampling probe when said top piece and said bottom piece are assembled together;
    whereby said mold cavity is filled with a quantity of powder and the powder is formed into one of a tablet and a caplet when the powder is compressed within said mold cavity by the punch.

2. The powder sampling and compaction die according to claim 1, wherein the powder sampling and compaction die has a longitudinal axis, and wherein said top piece has a top surface and a bottom surface, said top surface of said top piece has a contour which follows a portion of a cylindrical surface of an imaginary cylinder having a longitudinal axis which is parallel to said longitudinal axis of the powder sampling and compaction die, said bottom surface of said top piece abuttingly contacts said top surface of said bottom piece when said top piece and said bottom piece are assembled together, said top opening is defined by said passage intersecting said top surface of said top piece, and said bottom opening is defined by said passage intersecting said bottom surface of said top piece.

3. The powder sampling and compaction die according to claim 2, wherein said passage has a uniform cross sectional area in plan view such that the punch can be used to eject the one of a tablet and a caplet from said passage after said bottom piece is removed from said top piece.

4. The powder sampling and compaction die according to claim 3, wherein said passage is substantially circular in plan view such that the quantity of powder forms a tablet which is circular in plan view after the quantity of powder is compacted in said mold cavity.

5. The powder sampling and compaction die according to claim 3, wherein said passage is elongated with rounded ends in plan view such that the quantity of powder forms a caplet after compaction in said mold cavity.

6. The powder sampling and compaction die according to claim 3, wherein said top piece has a pair of holes, each of said pair of holes opening to said bottom surface of said top piece, the powder sampling and compaction die further including:
    a pair of rubber bushings each inserted in a respective one of said pair of holes, each of said pair of rubber bushings being friction fit within said respective one of said pair of holes; and
    a pair of pegs projecting from said top surface of said bottom piece, said pair of pegs being positioned such that each of said pair of pegs is received within a respective one of said pair of rubber bushings in friction fit with said respective one of said pair of rubber bushings when said top piece and said bottom piece are assembled together,
    said pair of holes formed in said top piece, said pair of rubber bushings, and said pair of pegs constituting said means for releasably securing said bottom piece to said top piece.

7. The powder sampling and compaction die according to claim 3, wherein said top piece has a first pair of holes which are threaded, each of said first pair of holes opening to said bottom surface of said top piece, said bottom piece has a second pair of holes extending from said bottom surface of said bottom piece to said top surface of said bottom piece, each of said second pair of holes being in registry with a respective one of said first pair of holes when said top piece and said bottom piece are assembled together, the powder sampling and compaction die further including:
    a pair of screws each extending through a respective one of said second pair of holes and threadedly engaging a respective one of said first pair of holes to thereby releasably secure said bottom piece to said top piece when said top piece and said bottom piece are assembled together,
    said first pair of holes formed in said top piece, said second pair of holes formed in said bottom piece, and said pair of screws constituting said means for releasably securing said bottom piece to said top piece.

8. A powder sampling and compaction die comprising:

a top piece having a thickness and a passage extending through said thickness, said passage having a top opening and a bottom opening, at least said top opening being adapted for allowing at least a portion of a punch to pass through said top opening and project into said passage;

a bottom piece having a top surface and a bottom surface; and means for releasably securing said bottom piece to said top piece such that said passage and said top surface of said bottom piece cooperatively form a mold cavity;

wherein said top piece has a pair of holes, the powder sampling and compaction die further including:

a pair of rubber bushings each inserted in a respective one of said pair of holes, each of said pair of rubber bushings being friction fit within said respective one of said pair of holes; and a pair of pegs projecting from said top surface of said bottom piece, said pair of pegs being positioned such that each of said pair of pegs is received within a respective one of said pair of rubber bushings in friction fit with said respective one of said pair of rubber bushings when said top piece and said bottom piece are assembled together, said pair of holes formed in said top piece, said pair of rubber bushings, and said pair of pegs constituting said means for releasably securing said bottom piece to said top piece;

whereby said mold cavity is filled with a quantity of powder and the powder is formed into one of a tablet and a caplet when the powder is compressed within said mold cavity by the punch.

* * * * *